United States Patent
Corbitt, Jr. et al.

(10) Patent No.: US 6,638,308 B2
(45) Date of Patent: *Oct. 28, 2003

(54) BIOABSORBABLE BREAST IMPLANT

(76) Inventors: John D. Corbitt, Jr., 2868 Kirkwood Village, Palm Springs, FL (US) 33461; Lori A. Leonetti, 5255 Montery Cir., #75, Delray Beach, FL (US) 33484

(*) Notice: Subject to any disclaimer, the term of this patent is extended or adjusted under 35 U.S.C. 154(b) by 80 days.

This patent is subject to a terminal disclaimer.

(21) Appl. No.: 09/828,806

(22) Filed: Apr. 10, 2001

(65) Prior Publication Data

US 2001/0041936 A1 Nov. 15, 2001

Related U.S. Application Data

(63) Continuation-in-part of application No. 09/169,351, filed on Oct. 9, 1998, now Pat. No. 6,214,045.
(60) Provisional application No. 60/091,306, filed on Jun. 30, 1998, provisional application No. 60/077,639, filed on Mar. 11, 1998, and provisional application No. 60/061,588, filed on Oct. 10, 1997.

(51) Int. Cl.[7] ............................................. A61F 2/12
(52) U.S. Cl. ..................................... 623/8; 424/400
(58) Field of Search ........................... 623/7, 8, 17.12, 623/23.71, 23.75, 23.76; 424/400

(56) References Cited

U.S. PATENT DOCUMENTS

| 4,298,998 A | | 11/1981 | Naficy ........................... 3/36 |
| 4,428,082 A | | 1/1984 | Naficy |
| 4,470,160 A | | 9/1984 | Cavon |
| 4,740,208 A | | 4/1988 | Cavon |
| 5,120,802 A | * | 6/1992 | Mares et al. ................... 64/18 |
| 5,522,896 A | | 6/1996 | Prescott ........................ 623/16 |
| RE35,391 E | | 12/1996 | Brauman ....................... 623/8 |
| 5,626,611 A | | 5/1997 | Liu et al. ...................... 606/230 |
| 5,824,081 A | | 10/1998 | Knapp et al. ................. 623/11 |
| 5,869,080 A | | 2/1999 | McGregor et al. ........... 424/426 |
| 5,922,024 A | | 7/1999 | Janzen et al. ................. 623/8 |
| 6,066,325 A | | 5/2000 | Wallace et al. ............... 424/400 |
| 6,214,045 B1 | * | 4/2001 | Corbitt, Jr. et al. ........... 623/8 |
| 6,316,522 B1 | * | 11/2001 | Loomis et al. ............... 523/105 |
| 6,403,758 B1 | * | 6/2002 | Loomis ........................ 528/354 |

FOREIGN PATENT DOCUMENTS

| EP | 0475 077 B1 | 3/1992 |
| EP | 0475 077 A2 | 3/1992 |
| WO | WO 94/16647 | 8/1994 |

OTHER PUBLICATIONS

P. Eisølt, "Development of Technologies Aiding Large—Tissue Engineering", *Biotechnol. Prog.*, vol. 14, No. 1, pp. 134–140, 1998.

* cited by examiner

*Primary Examiner*—David H. Willse
*Assistant Examiner*—Suzette J. Jackson
(74) *Attorney, Agent, or Firm*—Dickstein Shapiro Morin & Oshinsky, LLP

(57) ABSTRACT

A breast implant has at least an outer shell which is composed of a resorbable material. The implant, which can be formed entirely of bioresorbable material such as a collagen foam, is sized and shaped to replace excised tissue. The implant supports surrounding tissue upon implantation, while allowing for in-growth of fibrous tissue to replace the implant. According to various alternative embodiments, the implant is elastically compressible, or can be formed from self-expanding foam or sponges, and can be implanted through a cannula or by injection, as well as by open procedures. The implant can carry therapeutic and diagnostic substances.

6 Claims, 1 Drawing Sheet

BIOABSORBABLE BREAST IMPLANT

This application is a continuation-in-part of U.S. patent application Ser. No. 09/169,351 filed Oct. 9, 1998, now U.S. Pat. No. 6,214,045 which claimed the benefit of U.S. Provisional Application Serial No. 60/061,588, filed Oct. 10, 1997, U.S. Provisional Application Serial No. 60/077,639, filed Mar. 11, 1998, and U.S. Provisional Application Serial No. 60/091,306, filed Jun. 30, 1998, the disclosures of which are incorporated herein by reference.

BACKGROUND OF THE INVENTION

1. Field of the Invention

The present invention relates to implantable prostheses. More particularly, the present invention relates to implantable breast prostheses designed to eliminate encapsulation and reduce scarring, and to replace tissue removed for purposes of biopsy or lumpectomy.

2. Description of the Related Art

Breast prostheses are utilized for augmentation mammoplasty and in cosmetic surgery. Prostheses also are indicated in breast cancer surgery, such as lumpectomies, where a portion of the breast is removed and can leave some disfigurement if not replaced by a similar amount of tissue and/or augmentation material.

Similarly, biopsies can leave small dimples or imperfections if remedial steps are not taken. About 1 million breast biopsies are performed in the United States annually. As a result, some 200,000 new breast cancers are diagnosed each year.

Known methods of augmentation mammoplasty utilize silicone or saline implants. These methods have been complicated post-operatively by encapsulation of the implants, which can occur to varying degrees. Encapsulation produces a hard area of scar tissue around the implant, resulting in a rigid, abnormally-shaped mound beneath the breast tissue or pectoralis muscle, depending upon the placement of the implant.

Moreover, the known implant materials may not be indicated for replacement of smaller amounts of tissue, as would be required to prevent dimpling after biopsies, for example. Further, the known implant materials are not amenable to resizing. In addition, known implants are not capable of being implanted through a cannula or needle, and are not readily instilled with medicaments or chemical agents that would be useful in treating the patient.

Accordingly, a need exists for implants and methods that can be adapted for replacement of small as well as large amounts of tissue. A need also exists for implants that can be delivered through cannulae or needles, as well as being able to significantly reduce or eliminate encapsulation, resulting in a prolonged, aesthetically pleasing, soft mound below the breast tissue or pectoralis muscle. In addition, a need exists for implants into which useful substances, such as beneficial medications, chemical agents, hormonal treatments, stem cells, such as adipocytes, cellular precursors and components, and radiation media can be instilled to enhance the treatment capabilities of the implant in cancer and other breast pathology.

SUMMARY OF THE INVENTION

The present invention overcomes deficiencies of the prior art, such as those noted above, by providing an implant in which at least the outer portion of the implant, and as much as the entire implant, is made of a resorbable material. The implant is sized and shaped to replace excised tissue. Preferably, the implant provides a support structure in the form of a framework or scaffold for the surrounding tissue after implantation. The support structure preferably is porous to permit the in-growth of fibrous replacement tissue. Advantageously, replacement tissue in-growth takes place without encapsulation and with reduced scarring.

According to an embodiment of the invention, excised tissue is replaced by installing an implant having at least an outer shell of resorbable material. The implant is sized and shaped to replace the excised tissue. The implant supports surrounding tissue while fibrous tissue replaces the resorbable portion of the implant.

In a further development, at least a portion of the implant can be provided in the form of a compressible or non-compressible sponge or foam, or a self-expanding sponge or foam. The sponge or foam provides a porous support matrix for surrounding and in-growing tissue. In the form of a compressible, expandable, or self-expanding sponge or foam, the implant advantageously can be inserted through a cannula or a needle, or optionally can be directly inserted. Additionally, the implant can be instilled with beneficial materials, such as indicated medicaments, therapeutics, or diagnostic agents, as well as matrix enhancing additives.

Other features and advantages of the present invention will become apparent from the following description of the invention which refers to the accompanying drawings.

DETAILED DESCRIPTION OF THE PREFERRED EMBODIMENTS

Figure 1:
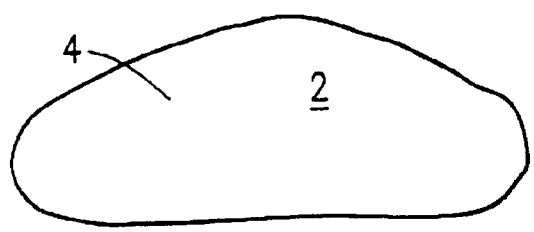
FIG. 1 is a schematic elevation of a breast implant according to a preferred embodiment of the present invention.
Figure 2:
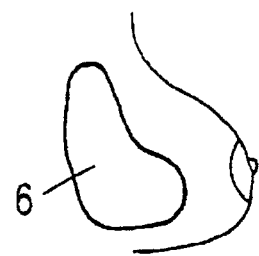
FIG. 2 is a schematic sectional view of a breast after implantation of the implant of FIG. 1.

Referring initially to FIGS. 1 and 2, an implant 2 has an outer shell 4 made of a biosorbable material woven into a mesh. The inner contents of the implant are fluids such as saline and autologous blood products.

Outer shell 4 is made entirely of biosorbable materials, such as collagens or polyglycolic acids, for example. Over a period of approximately three weeks to six months, the outer shell dissolves, leaving the inner contents 6 present inside the breast. Hard encapsulation will not occur because there is not a foreign body contained within the prosthetic space.

Figure 3:
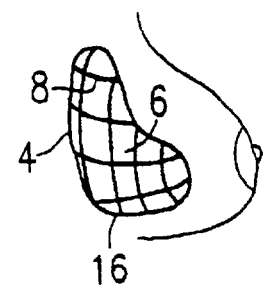
FIG. 3 is a schematic sectional view of a breast after implantation of an alternative embodiment of the implant of the present invention.

Referring to FIG. 3, implantation of an alternative embodiment of implant 2 is illustrated in which the outer shell 4 includes both biosorbable material, and nonabsorbable material, such as monofilament polypropylene fibers. Outer shell 4 is provided as a mesh or weave of the mixed material, surrounding contents 6 as described above. After a resorption period, contents 6 remain surrounded by a skeletal outer shell made up of non-absorbable fibers 8.

Advantageously, the proportions and spacing of the two types of materials can be altered to provide the desired properties of containment using a minimal amount of non-absorbable material. Accordingly, the non-absorbable fibers 8 which remain after the biosorbable materials resorb will act as a scaffolding to allow the prosthesis to hold its shape; however, because of the limited amount of foreign material, encapsulation and scarring are decreased.

Figure 4:
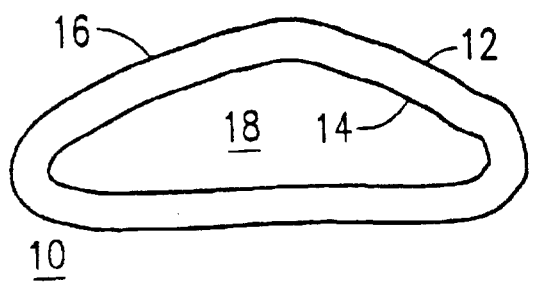
FIG. 4 is a schematic sectional view of a breast implant according to a second alternative embodiment of the present invention.
Figure 5:
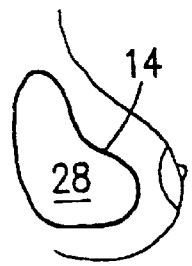
FIG. 5 is a schematic sectional view of a breast after implantation of the implant of FIG. 4.

Referring to FIGS. 4 and 5, a second alternative embodiment of the present invention is shown. A prothesis 10 features two capsules, a larger, outer capsule 12 made of biosorbable materials, and a smaller inner capsule 14 made of a non-absorbable material. Inner capsule 14 also can be made partially resorbable as in the first alternative embodiment above. Outer capsule 12 and inner capsule 14 can be separated by a thin layer 16 of saline or autologous fluids such as those described above. Inner capsule 14 surrounds a more permanent prosthesis 18 made of autologous fluids or saline, for example.

After implantation, outer capsule 12 dissolves, thus preventing hardening by encapsulation of the prosthesis. The supply of fluid 16 between the capsules (a few to several cc.'s) is absorbed by the body once released by the dissolution of outer capsule 12.

Figure 6:
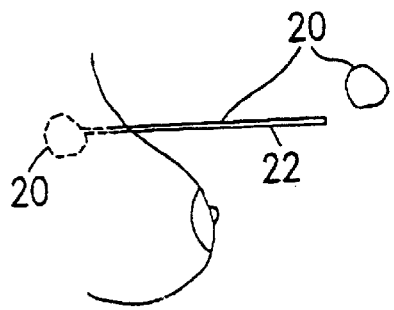
FIG. 6 is a schematic sectional view of a breast implant and a method of insertion according to further alternative embodiments of the present invention, particularly for cases involving the removal of smaller pieces of tissue such as by biopsy and lumpectomy.

Referring to FIG. 6, a further alternative embodiment of the present invention includes an implant prosthesis 20 provided in the form of a matrix framework, such as a sponge or foam. The implant, which preferably is entirely biodegradable (resorbable), has a porous structure which supports the surrounding tissue and provides a framework for the in-growth of fibrous tissue material.

According to a preferred embodiment, the implant is provided in the form of a foam or sponge which can be modified by a surgeon prior to implantation, such as at a lumpectomy or biopsy site, simply by trimming the sponge to the appropriate size and shape. Alternatively, the implant can be a pre-shaped prosthesis of appropriate size, or an appropriate amount of foam or foam-forming materials. Optionally, the foam can be provided as a self-expanding matrix that either is compressed, or forms in situ. Advantageously, the implant can be modified to correspond to the breast tissue that either has been removed, requires replacement, or requires augmentation. The foam or sponge matrix is sufficiently resilient to support the surrounding tissue without collapsing.

A preferred method of implantation is illustrated schematically in FIG. 6, whereby the implant is elastically compressible, and is delivered using a cannula or needle 22 inserted into the breast. A single implant 20 is shown being compressed so as to fit within cannula 22. A force is applied to drive the compressed implant distally through and out the distal end of the cannula into the implant site, where the resilient implant 20 expands to fill the implant site space.

The force for advancing the sponge or foam material through the cannula can be applied directly to the implant, or indirectly using fluids, for example. Advantageously, the implant can be used in conjunction with stereotactic biopsy instrumentation, such as the ABBI® System, the MIB System by US Surgical, or the Mammotome® System by Johnson and Johnson.

As a further alternative, the sponge or foam implant of the present invention can form all or part of a larger implant, such as those described above. Accordingly, the tissue supporting sponge or foam matrix will form, for example, all or part of the outer shell 4 of implant 2. Implantation using open procedures usually would be indicated when the sponge implant of the present invention is used as all or part of a larger implant. Accordingly, the sponge or implant would be placed directly into the biopsy or lumpectomy cavity.

In addition, the implant 20 can be provided in the form of a self-expanding foam, which can be injected by needle or through cannula 22 in a metered amount. An appropriate amount of foam-forming materials can be inserted through cannula 22 and allowed to expand or form a matrix within the cavity created by the excised tissue. Alternatively, a specialized applicator may be used to inject the desired amount of the foam. The amount of foam is preselected to allow sufficient expansion to fill the void left by the excision and support the surrounding tissue to prevent dimpling.

Following insertion of the implant, such as by an open method or one of the stereotactic methods described above, the resorbable implant occupies the breast tissue cavity and supports the surrounding tissue until such time as it resorbs or biodegrades. After initial implantation, the patient's own fluids, fibroblast, and stem cells, such as adipocytes, vascular stem cells, and others, permeate the sponge prosthesis. In the case of a small implant, such permeation would occur naturally, subsequent to implantation. In the case of a larger implant, providing the implant at least partially filled with fluids prior to implantation may be indicated.

Advantageously, the new prosthesis decreases encapsulation after implantation. Various biosorbable materials can be used in the implant of the present invention. Known biosorbable materials include polyglycolic acid (Dexon, Davis & Geck); polyglactin material (Vicryl, Ethicon); poliglecaprone (Monocryl, Ethicon); and synthetic absorbable lactomer 9-1 (Polysorb, United States Surgical Corporation).

Other foamable materials that can be utilized in the present invention include, without limitation, proteins such as collagen, fibronectin, laminin and fibrin, most preferably collagen, and high molecular weight polysaccharides, such as heparan sulphate, chondroitin sulphate, hylauronic acid and dermatan sulphate. Mixtures of any of the aforementioned materials also can be used, as required.

The materials can be modified, by cross-linking for example, to control degradation rates over varying lengths of time, after which they are substantially or completely resorbed.

Foams can be formed by various means known to those skilled in the art, including injecting an aerosol into a gel, and freeze-drying aqueous dispersions of the foam-forming material. Foaming agents can be included to promote formation of the foam. In addition, stabilizing agents can be included to enhance foam stability. The foams can be extruded or formed in situ.

According to the present invention, these products may be mixed with one another or combined to provide various resorption times or gradients, and/or may be interrelated with non-absorbable materials, such as polypropylene or PTFE (Gortex) material, for example. In an instance where a non-absorbable material is utilized, the non-resorbable implant section will remain partially intact as a permanent structure.

In each of the embodiments, the resorbable portions of the prosthesis ultimately biodegrades, and the patient is left with autologous tissue, some of which may have been implanted, or a permanent implant such as saline, as a filler for the biopsy cavity, thus preserving the contour of the breast and preventing indentation of the overlying skin.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An implant for implantation in a human body comprising an outer shell of a resorbable material comprising collagen, the implant being formed to fit the shape and size of a cavity in the human body, the implant supporting tissue surrounding the cavity upon implantation and allowing for in-growth of fibrous tissue into and replacing the outer shell, and a resorbable core provided inside and surrounded by the outer shell and containing autologous material.

2. The implant of claim 1, wherein the core is partially enclosed by a nonabsorbable material.

3. A breast implant comprising a matrix of protein material, the matrix comprising a foam having a porous structure for supporting surrounding tissue of a breast and configured to provide a framework for the in-growth of fibrous tissue into the matrix.

4. The breast implant of claim 3, wherein the protein material is selected from the group consisting of collagen, fibronectin, laminin, and fibrin.

5. A breast implant comprising a matrix of protein material and having a porous structure for supporting surrounding tissue of a breast and configured to provide a framework for the in-growth of fibrous tissue into the matrix, wherein the matrix is self-expanding.

6. The breast implant of claim 5, wherein the protein material is selected from the group consisting of collagen, fibronectin, laminin, and fibrin.

* * * * *